US012569227B2

(12) United States Patent
Duncan

(10) Patent No.: US 12,569,227 B2
(45) Date of Patent: Mar. 10, 2026

(54) ULTRASOUND BEAMFORMER-BASED CHANNEL DATA COMPRESSION

(71) Applicant: Siemens Medical Solutions USA, Inc., Malvern, PA (US)

(72) Inventor: David P. Duncan, Renton, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2 days.

(21) Appl. No.: 18/314,855

(22) Filed: May 10, 2023

(65) Prior Publication Data

US 2023/0270417 A1 Aug. 31, 2023

Related U.S. Application Data

(62) Division of application No. 14/726,015, filed on May 29, 2015, now Pat. No. 11,684,346.

(51) Int. Cl.
| | |
|---|---|
| *A61B 8/00* | (2006.01) |
| *G01S 7/52* | (2006.01) |
| *G01S 15/89* | (2006.01) |
| *G10K 11/34* | (2006.01) |

(52) U.S. Cl.
CPC .......... *A61B 8/5246* (2013.01); *A61B 8/5207* (2013.01); *G01S 7/52034* (2013.01); *G10K 11/346* (2013.01); *A61B 8/488* (2013.01); *G01S 15/8915* (2013.01)

(58) Field of Classification Search
None
See application file for complete search history.

(56) References Cited

U.S. PATENT DOCUMENTS

| | | | |
|---|---|---|---|
| 5,971,923 | A | 10/1999 | Finger |
| 6,042,545 | A | 3/2000 | Hossack et al. |
| 6,450,959 | B1 | 9/2002 | Mo et al. |
| 8,157,738 | B2 | 4/2012 | Wegener et al. |
| 8,317,706 | B2 | 11/2012 | Wegener |
| 8,428,378 | B2 | 4/2013 | Mansour |
| 8,666,123 | B2 | 3/2014 | Gossweiler et al. |
| 2003/0097068 | A1 | 5/2003 | Hossack et al. |
| 2003/0149357 | A1 | 8/2003 | Liu |

(Continued)

FOREIGN PATENT DOCUMENTS

| | | | | |
|---|---|---|---|---|
| WO | 1997009930 A1 | 3/1997 | | |
| WO | WO-0016308 A1 | * | 3/2000 | ........... G10K 11/341 |
| WO | 2000030544 A1 | 6/2000 | | |

OTHER PUBLICATIONS

Cheng, Po-Wen, Che-Chou Shen, and Pai-Chi Li. "MPEG compression of ultrasound RF channel data for a real-time software-based imaging system." IEEE transactions on ultrasonics, ferroelectrics, and frequency control 59.7 (2012): 1413-1420.

(Continued)

*Primary Examiner* — Christopher Koharski
*Assistant Examiner* — Farouk A Bruce

(57) ABSTRACT

Ultrasound beamformer-based channel data compression allows for software-based image formation. To increase the amount of data transferred, ultrasound beamformer-based channel data compression is provided. A beamformer is used to compress instead of or in addition to traditional beamformation. The compression reduces the data bandwidth while allowing reconstruction of the original channel data.

19 Claims, 4 Drawing Sheets

(56) References Cited

U.S. PATENT DOCUMENTS

| | | | |
|---|---|---|---|
| 2003/0149362 A1 * | 8/2003 | Azuma | G01S 7/52047 |
| | | | 600/437 |
| 2006/0106309 A1 * | 5/2006 | Liu | G01S 7/52095 |
| | | | 600/447 |
| 2006/0159195 A1 * | 7/2006 | Ionescu | H04L 1/065 |
| | | | 375/267 |
| 2006/0173313 A1 * | 8/2006 | Liu | G01S 15/8993 |
| | | | 600/437 |
| 2007/0016022 A1 | 1/2007 | Blalock et al. | |
| 2007/0073152 A1 | 3/2007 | Washburn | |
| 2008/0114246 A1 | 5/2008 | Randall et al. | |
| 2010/0063399 A1 * | 3/2010 | Walker | G01S 7/52026 |
| | | | 600/459 |
| 2010/0305449 A1 | 12/2010 | Wegener et al. | |
| 2010/0331689 A1 * | 12/2010 | Wegener | G01S 7/52034 |
| | | | 600/443 |
| 2011/0074792 A1 | 3/2011 | Li | |
| 2012/0143059 A1 * | 6/2012 | Magee | G01S 7/52047 |
| | | | 600/447 |
| 2013/0109971 A1 | 5/2013 | Dahl et al. | |
| 2013/0245441 A1 | 9/2013 | Datta | |
| 2013/0296703 A1 | 11/2013 | Wel et al. | |
| 2014/0334266 A1 * | 11/2014 | Cogan | G01S 7/5208 |
| | | | 367/138 |
| 2015/0025378 A1 * | 1/2015 | Susumu | G01S 7/52047 |
| | | | 600/437 |
| 2016/0174941 A1 | 6/2016 | Ho et al. | |

OTHER PUBLICATIONS

Li, Yen-Feng, and Pai-Chi Li. "Ultrasound beamforming using compressed data." IEEE Transactions on Information Technology in Biomedicine 16.3 (2012): 308-313.

Sharmin Kibria, "Optimal Basis for Ultrasound Rf Apertures: Applications to Real-Time Compression and Beamforming", Masters Theses 1911, University of Massachusetts Amherst Feb. 2014. pp. 1-62.

Chernyakova T. Ez Al; "Fourier-Domain Beamforming: The Path to Compressed Ultrasound Imaging"; IEEE Transactions on Ultrasonics, Ferroelectrics, and Frequency Control; vol. 61; No. 8; Aug. 2014; pp. 1252-1267.

* cited by examiner

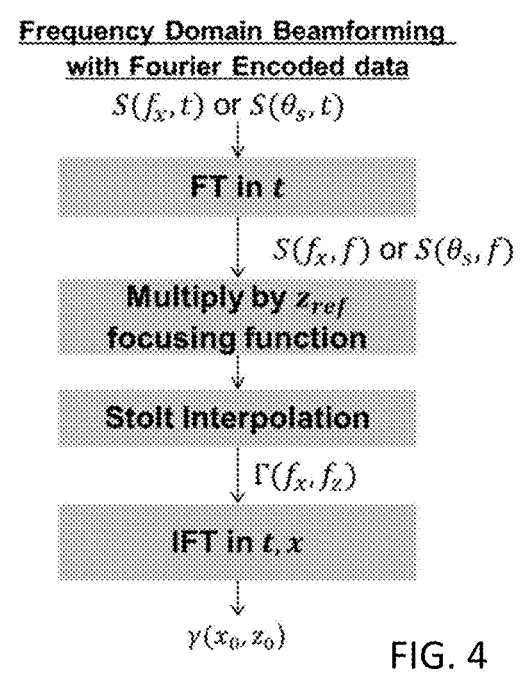

Frequency Domain Beamforming
with Fourier Encoded data

$$S(f_x, t) \text{ or } S(\theta_s, t)$$

FT in $t$ $$S(f_x, f) \text{ or } S(\theta_s, f)$$

Multiply by $z_{ref}$
focusing function

Stolt Interpolation $$\Gamma(f_x, f_z)$$

IFT in $t, x$ $$\gamma(x_0, z_0)$$

FIG. 4

ULTRASOUND BEAMFORMER-BASED CHANNEL DATA COMPRESSION

RELATED APPLICATION

This application is a divisional of U.S. application Ser. No. 14/726,015, filed May 29, 2015, which is hereby incorporated by reference in its entirety.

BACKGROUND

The present embodiments relate to medical diagnostic ultrasound imaging. In particular, channel data compression is provided for ultrasound imaging using software.

As computer processing power increases, ultrasound systems have been gradually transferring hardware signal processing functionality into software. Software-based signal processing is advantageous for flexible development, better maintainability, cost, and quick experimentation. The primary problem facing a software-based ultrasound system is getting large amounts of single-element, raw channel data from an ultrasound front-end into a computer memory for processing. When the system channel count is high (e.g., 128 elements or channels), transfer data rates may be extremely high and challenge the maximum data rates of even the most state of the art computer bus. To deal with such large transfer rates, additional or custom hardware may be used, but this defeats the primary purpose of hardware reduction. The maximum acoustic frame rate and/or the number of channels may be reduced, but this results in decreased image quality.

BRIEF SUMMARY

By way of introduction, the preferred embodiments described below include methods, computer readable media, instructions, and systems for ultrasound imaging. To increase the amount of data transferred, ultrasound beamformer-based channel data compression is provided. A beamformer is used to compress instead of or in addition to traditional beamformation. The compression reduces the data bandwidth while allowing reconstruction of the original channel data.

In a first aspect, a system is provided for ultrasound imaging. A transmit beamformer is configured to transmit first beams for a first imaging mode and second beams for a second imaging mode. A transducer includes elements for receiving acoustic echoes in response to the first and second beams. A receive beamformer is configured to receive electrical signals from the elements, to beamform samples from the electrical signals responsive to the first beams, and to compress the electrical signals responsive to the second beams using a Fourier transform applied across the elements for each time. A processor is configured to generate imaging information for the first imaging mode from beamformed samples and to generate imaging information for the second imaging mode from the compressed electrical signals.

In a second aspect, a method is provided for ultrasound beamformer-based channel data compression. Channel data is received from elements of a transducer array. The channel data is encoded laterally across the array with a delay and sum beamformer with a set of basis functions. The basis functions reduce the amount of data to send over a computer bus and enable recovery of the channel data from the output of a decoding operation. The basis set encoding is repeated for new frames of channel data and the output of the encoding is transmitted over the computer bus.

In a third aspect, a method is provided for ultrasound beamformer-based channel data compression. A plurality of channels of element signals is sampled. A receive beamformer transforms samples from the sampling domain into frequency data in a spatial frequency domain. The frequency data is inverse transformed. A processor generates an ultrasound image from an output of the inverse transforming.

Further aspects and advantages of the invention are discussed below in conjunction with the preferred embodiments. The present invention is defined by the following claims, and nothing in this section should be taken as a limitation on those claims.

BRIEF DESCRIPTION OF THE DRAWINGS

The components and the figures are not necessarily to scale, emphasis instead being placed upon illustrating the principles of the invention. Moreover, in the Figures, like reference numerals designate corresponding parts throughout the different views.

FIG. 4 is an example process for frequency domain beamforming with Fourier encoded channel data from a beamformer.

DETAILED DESCRIPTION OF THE DRAWINGS AND PRESENTLY PREFERRED EMBODIMENTS

Ultrasound raw channel data is compressed for transmission to a processor or system for ultrasound imaging. Any basis function set, such as a Fourier basis, may be used. The compression is achieved in the lateral dimension or across the array, allowing use of a conventional delay-and-sum beamformer. When the number of frequency domain 'beams' or amount of frequency domain data representing the channel data is less than the number of channels, an effective compression is achieved compared to directly transferring raw channel data. Raw channel data compression of 3:1 or more may be provided. Commonly used hardware (i.e., a delay-and-sum beamformer) performs lateral encoding of the raw channel data to reduce the total amount of raw channel data sent over the PCIExpress or other bus to a computer.

This re-use of existing hardware may keep development time and costs low and/or allow the use of new beamforming technologies, such as frequency domain beamforming applied in software. For Fourier beamforming, the beamformer-created Fourier data may be Fourier transformed over time or depth, providing a two-dimensional transform of the channel data. Beamformation may then be provided in the two-dimensional Fourier domain.

In one embodiment, multiple channels of raw data from a transmission event are sampled and sent to a hardware delay-and-sum beamformer. The beamformer applies a combination of complex apodization weights and/or lateral delay profiles that allow the beamformer to form 'beams' in the frequency space of the raw channel data, effectively Fourier encoding the data. Other apodization and/or delay profiles may be used to implement other basis functions that substantially enable recovery of channel information. Lossless or lossy recovery of the channel data may be used or the data may be further transformed for beamforming from a domain other than the spatial-temporal domain of the channel data.

Since a beamformer is used for compression, the same beamformer may be used for conventional delay-and-sum beamformation. The beamformer operates "on the fly" to switch between encoding for compression (i.e., channel basis function encoding) and conventional beamformation. For example, data from one imaging mode (e.g., B-mode) is Fourier encoded and compressed for high-quality, low-data rate imaging to be provided while data from another imaging mode (e.g., flow or color mode) is beamformed conventionally for typical image processing. Alternatively, in other modes, the beamformer is bypassed completely, allowing uncompressed raw channel data to be collected and processed entirely using software-based beamformation.

Figure 1:
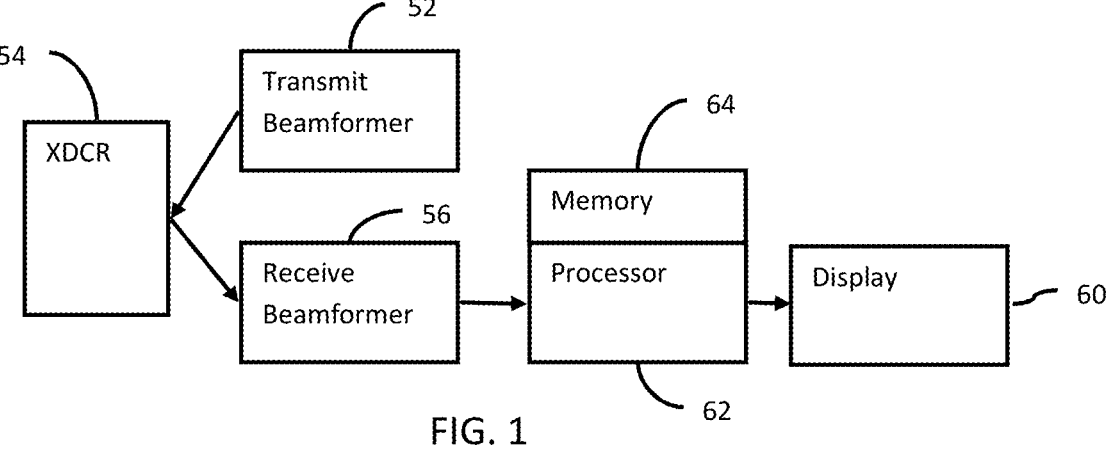
FIG. 1 is a block diagram of one embodiment of a system for ultrasound imaging.

FIG. 1 shows one embodiment of a system for ultrasound imaging. The system performs the method described below for FIG. 4 or 5 or a different method. The system operates using both conventional beamformation and compression of channel data by the receive beamformer 56. In other embodiments, the system only operates using the compression of channel data by the receive beamformer 56. Alternatively, the system performs any beamforming with the processor 62 and uses the receive beamformer 56 for compression.

The ultrasound system includes a transmit beamformer 52, a transducer 54, a receive beamformer 56, a display 60, a processor 62, and a memory 64. Other systems may be used. Additional, different or fewer components may be provided. For example, a detector and/or scan converter are provided. As another example, a user input device (e.g., mouse and/or keyboard) is provided for accepting user selection of an imaging application (e.g., cardiac imaging) and/or other configuration, such as a selection of imaging parameters. In yet another example, the transmit beamformer 52, transducer 54, and/or display 60 are not provided, such as where raw channel data is provided from any source for compression and transfer to the processor 62 with or without more processing.

The system is a medical diagnostic ultrasound imaging system. Imaging includes two-dimensional, three-dimensional, B-mode, Doppler, color flow, spectral Doppler, M-mode, strain, elasticity, harmonic, contrast, or other imaging modalities now known or later developed. The ultrasound system is a full size cart mounted system, a smaller portable system, a hand-held system, or other now known or later developed ultrasound imaging system. In another embodiment, the processor 62 and memory 64 are part of a separate system. For example, the processor 62 and the memory 64 are a workstation or personal computer operating independently of or connected with the beamformers 52, 56.

The transmit beamformer 52 is one or more waveform generators, amplifiers, delays, phase rotators, multipliers, summers, digital-to-analog converters, filters, combinations thereof, and other now known or later developed transmit beamformer components. The transmit beamformer 52 is configured into a plurality of channels for generating transmit signals for each element of a transmit aperture. The transmit signals for each element are delayed and apodized relative to each other for focusing acoustic energy along one or more scan lines. Delay is implemented as a temporal delay of a generated waveform, delay of generating a waveform, and/or phase shift of a waveform in generating or after being generated. Signals of the same or different amplitudes, frequencies, bandwidths, delays, spectral energy distributions or other characteristics are generated for one or more elements 70 of the transducer 54 during a transmit event.

The transmit beamformer 52 is configured to generate any number of beams. One or more beams may be generated at a same time. Each beam is focused along a transmit scan line to allow reception of a receive beam along the same scan line. A sequence of beams steered in any format (e.g., linear, Vector®, or sector) may be generated. A broad beam may be generated for receiving along a plurality of receive scan lines in response to the single transmit broad beam. Plane wave, diverging wave, or infinite focus may be used for the broad beam.

In one embodiment, the transmit beams are generated for each of multiple different imaging modes. For example, color, flow or Doppler-mode imaging and corresponding transmit beams are interleaved with B-mode imaging and corresponding transmit beams. Beam, group of beam, or frame interleaving may be used. During on-going or continuous scanning of a patient, the transmit beams for the different imaging modes are transmitted in an interleaved sequence. One or more beams for one imaging mode may also be used for the other imaging mode.

The transducer 54 is a one-dimensional, multi-dimensional, or other now known or later developed array of elements 70. Each element 70 of the transducer 54 is a piezoelectric, microelectromechanical, capacitive membrane ultrasound transducer, or other now known or later developed transduction element 70 for converting between acoustic and electrical energy. Each of the transducer elements 70 connect to the beamformers 52, 56 for receiving electrical energy from the transmit beamformer 52 and providing electrical energy responsive to acoustic echoes to the receive beamformer 56. In response to transmission of the transmit beams, acoustic echoes are received by the elements 70 and converted into electrical signals. These electrical signals from any of the elements 70 in the receive aperture are passed separately to the receive beamformer 56.

The receive beamformer 56 is configured to acquire ultrasound data representing a region of a patient. Electrical signals representing the acoustic echoes from a transmit event are passed to the channels of the receive beamformer 56. In one embodiment, the receive beamformer 56 is formed from one or more application specific integrated circuits, processors, controllers, or other integrated circuits. The receive beamformer 56 includes a plurality of channels for separately processing signals received from different elements of the transducer 54. Each channel may include delays, phase rotators, amplifiers, filters, multipliers, summers, analog-to-digital converters, control processors, combinations thereof, or other now known or later developed receive beamformer components. The receive beamformer 56 also includes one or more summers for combining signals from different channels into a beamformed signal. A subsequent filter may also be provided. Other now known or later developed receive beamformers may be used.

Figure 2:
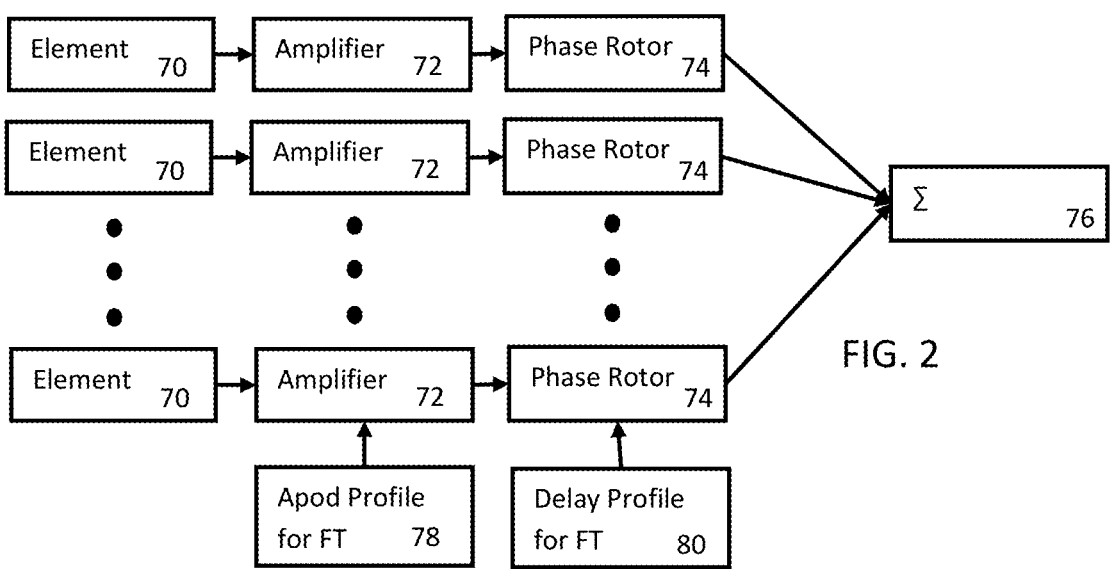
FIG. 2 is a block diagram of one embodiment of a receive beamformer for ultrasound beamformer-based channel data compression.

FIG. 2 shows one embodiment of the receive beamformer 56 connected with elements 70 of an array. Each channel of the receive beamformer 56 connects with one element 70, but may connect with more than one element 70 and/or different elements 70 through a multiplexer. Any number of channels is provided. Each channel includes an amplifier 72 and a phase rotator 74. Other amplification devices or circuits may be used. The delay for the delay-and-sum beamformer 56 may be implemented with other devices instead of or in addition to the phase rotator, such as a delay or buffer. The phase rotators 74 may be positioned prior to or after the amplifiers 72.

The amplifiers 72 are programmable to apply a desired amount of amplification. An apodization profile 78 is provided by a processor, memory, or controller. The apodization profile 78 provides for the same or different amplification by the different amplifiers 72. Relative weighting of one channel to the others is provided by the apodization profile 78.

The phase rotators 74 are programmable to apply a desired amount of phase shifting or other delay. A delay profile 80 is provided by a processor, memory, or controller. The delay profile 80 provides for the same or different phase shift by the different phase rotators 74. Relative phase rotation of one channel to the others is provided by the delay profile 80.

The summer 76 sums information from the channels in a given receive aperture. The summer 76 is a digital summer, but may be an analog summer. A single summer is provided to sum outputs from all of the channels. Alternatively, hierarchal summers or cascade of summers are used. At a given time or clock cycle, each channel outputs data, such as digital samples. The output data represents lateral position along a one or multi-dimensional array for the given time or clock cycle. The output data is relatively delayed and apodized based on the delay profile 80 and apodization profile 78. The summer 76 sums the outputs from the channels at each of a sequence of times.

Referring to FIGS. 1 and 2, the receive beamformer 56 receives electrical signals from the elements 70. The electrical signals are digitized or sampled. These samples are provided as channel data for each channel from respected elements 70. These samples are either beamformed or compressed. For example, samples for one mode of imaging are beamformed using conventional delay-and-sum beamformation based on the geometry of the elements 70 relative to the location in the patient for which the echo response is sampled. Samples for another mode of imaging are compressed. Rather than using the geometry of elements 70 to sample location, the apodization and/or delay profiles 78, 80 are based on basis function encoding for compression. A channel encoding operation is performed by the beamformer 56.

The switching between the modes is dynamic or on the fly. The switching may occur based on imaging conditions and imaging requirements (e.g., achievable compression ratio) and/or to optimize system performance (e.g., reduce the computational load). In one example, a B-mode/Color frame sequence is run on the ultrasound imaging system. The B-mode image is formed using broad beam transmissions (e.g. plane waves) to accomplish high-frame rate imaging, while conventional focused beam transmissions are used for the Color data to enhance imaging signal-to-noise ratio. In this example, B-mode images are formed using frequency domain beamforming, so it is more computationally efficient to Fourier encode the raw channel data using the beamformer 56 operating in the channel-encoding mode. While in the case of the color frame data, the beamformer forms image lines close to the areas where the focused transmissions are occurring. For these frames, the beamformer is operates in the conventional delay-and-sum operation. Other combinations of different modes may be used. The color data may be encoded, and the B-mode data may be conventionally beamformed. More than two modes of imaging may be used at a time.

For conventional beamforming, the receive beamformer 56 outputs in-phase and quadrature, radio frequency or other data representing one or more locations in a scanned region. The channel data is relatively weighted and delayed based on geometric relationship of element location to sample location in the patient. This weighting aligns the data output by the channels so that the data represents the same location in the patient. By summing the data, a beamformed sample representing the received echo from that location is formed. By repeating the process over time, a set of samples representing a beam along a scan line is formed. The receive beamformer 56 operates in the traditional delay-and-sum beamforming operation (i.e. generating image "lines").

For compression, the electrical signals responsive to the transmit beam or beams are processed by the receive beamformer 56. Instead of use array geometry and beamform focus location in the patient for the apodization and delay profiles 78, 80, a basis function for compression or encoding the channel data is applied with the profiles 78, 80. Rather than delaying the data so that the output to the summer 76 from each channel corresponds to echoes from the same location in the patient, the delays and apodization implement a basis function for compression or encode the data in a recoverable way.

Any complete basis function set may be used, such as a wavelet basis or a Fourier basis. The chosen basis functions transform the channel data into a different domain in which less data may represent the same or substantially same information. Substantially is used to account for lossy compression. By using basis function encoding, the channel data may be recovered, such as by applying an inverse transform operation.

In one embodiment, the receive beamformer 56 uses a Fourier transform applied across the elements for each time. At a given clock cycle, each channel is processing data received by the elements at a same time. Alternatively, relative delay may have been applied. The Fourier transform is applied to the channel data across channels or laterally. The Fourier transform spatially encodes the channel data between channels rather than over time (i.e., along depth).

The delay-and-sum beamforming operation is represented in a general form as:

$$b(t) = \int_x s(t - \tau(x), x)a(x)dx$$

where t is time, x is element position, s(t) is the raw channel data, $\tau(x)$ is the lateral-dependent delay profile, a(x) is the lateral apodization profile, and b(t) is the beamformed signal. In order to achieve lateral Fourier compression of the data using conventional delay-and-sum beamforming, the lateral-dependent delay profile and/or lateral apodization profile implement the basis function encoding for compression. The phase rotators or other delay elements and amplifiers with the summer implement the encoding. The resulting summation output by the beamformer is compressed channel data.

In one approach, the phase or delay profile for the geometric relationship is zero. No relative shift between elements is implemented based on the different distances or other geometrical relationship of the elements to the location in the patient. The apodization function is a complex apodization function. To implement the complex apodization, some phase shift may be applied by phase rotators or other delay elements. The only delay profile used is to implement the complex apodization function. Alternatively, a shift based on geometrical relationship is included, but an additional shift is provided for compression using the complex apodization profile.

In this approach, the beamforming profiles 78 and 80 provide for complex apodization. The delay profile of $\tau(x)=0$ is used, letting $a(x)=e^{j2\pi f_x x}$. This results in a Fourier transform across channels. The encoding is repeated for each time. For a two-dimensional Fourier transform, a further processor may transform along the temporal or depth direction, yielding:

$$B(f)=\int_x S(f,x)e^{-j2\pi f_x x}dx=S(f,f_x).$$

The spectrum of the beamformed or compressed data is equal to a single Cartesian line (along $f_x$) in the two-dimensional spectrum of the raw channel data. In other embodiments, the Fourier transform is not applied in the temporal or depth direction. Instead, the compressed data is provided to a processor and inverse compression is applied to reconstruct the channel data.

In another approach, a unity apodization function is applied by the amplifiers. The phase rotators or delays provide or add a linear delay profile for implementing compression laterally across the channels and corresponding elements 70. The linear delay profile is a function of the lateral position of the elements 70 and the steering angle of the receive beam and/or transmit beam. In this radial Fourier sampling approach, the beamformer apodization is chosen to be $a(x)=1$ and a linear delay profile of:

$$\tau(x) = \frac{x \tan \theta_s}{c}$$

is used where $\theta_s$ is the steering angle for the linear delay profile. As discussed above for the first approach, the Fourier transform is applied across the array. A further Fourier transform may later be applied, such as by the processor 62. Taking a Fourier transform in t (time or axially) gives:

$$B(f) = \int_x S(f, x)e^{-j2\pi f\frac{\tan\theta_s}{c}x}dx = S\left(f, f\frac{\tan\theta_s}{c}\right).$$

The one-dimensional beamformed spectrum maps directly onto a radial line in the two-dimensional spectrum of the raw channel data. The slope of the line is directly related to the received steering angle, but is not a 1:1 mapping as seen in the conventional Fourier-slice theorem.

Other approaches may be used. For example, the Fourier transform or other transform may use both the apodization and delay profile to implement the basis function encoding. The summation by the summer 76 completes the data encoding and compression. After applying the apodization and delay, the summation finishes the implementation of the basis function encoding.

The compression with eventual beamformation by the processor 62 is used for all ultrasound imaging by the system or only for some of the ultrasound imaging. In one embodiment, the imaging parameters and/or conditions are used to determine whether a given imaging mode uses compression or conventional beamformation. For example, the imaging mode with a higher imaging frequency, a greater field of view, greater frame rate, or other characteristic uses compression and other imaging mods use conventional beamformation by the beamformer. For a given mode, the compression ratio may be used to select between compression for transmission of data for software beamformation and no compression for transmission of the channel data for software beamformation.

The compression ratio indicates the effectiveness of compression as compared to passing channel data to a processor 62 for beamformation. Beamformation reduces the amount of data, but limits the usefulness of the data. By providing channel data to the processor 62, software-based image formation may be used. The compression ratio of uncompressed channel data to compressed channel data may be used to select which form of channel data to pass on.

The compression ratio is, for example, represented as:

$$CR = \frac{\text{uncompressed size}}{\text{compressed size}}$$

The Fourier compression is influenced primarily by the imaging parameters and/or conditions. The potential compression ratios may be calculated as a function of the main imaging parameters, such as f #, imaging frequency, acceptance angle, steering angle, aperture size, or others. When imaging with plane wave transmissions with a transmission angle of $\theta_T=0°$ and using a transducer of length L, the maximum lateral spatial frequency is given as:

$$f_{xh} = \frac{\sin \theta}{\lambda}$$

where $\theta$ is the reception angle and $\lambda$ is the wavelength. Using this expression plus the lateral frequency spacing of:

$$\Delta f = \frac{1}{L},$$

the number of frequency lines needed for Nyquist sampling is given as:

$$N_{lines} = \frac{2f_x}{\Delta f} = \frac{2L \sin \theta}{\lambda}.$$

The compression ratio is then calculated as:

$$CR = \frac{N_{channels}}{N_{lines}} = \frac{\lambda N_{channels}}{2L \sin \theta},$$

showing that the compression is dependent upon the imaging frequency, $1/\lambda$, and also upon the selected transducer acceptance angle, $\theta$.

Figure 3:
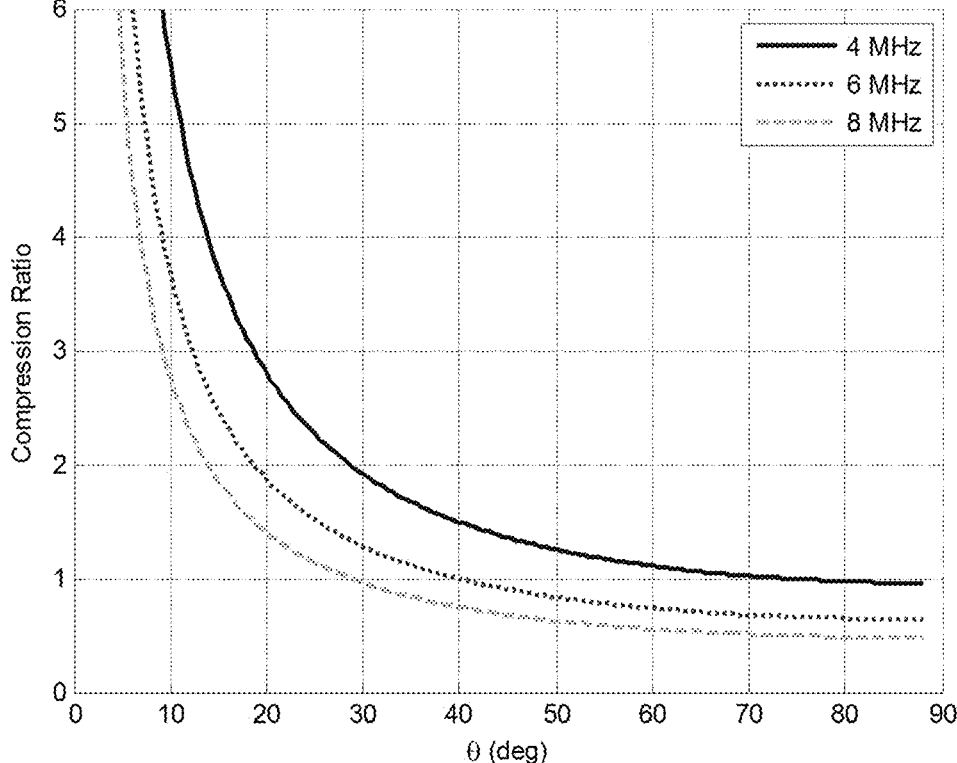
FIG. 3 is an example graph of compression ratio for Fourier transformation by a beamformer as a function of steering angle and frequency.

As an example, FIG. 3 shows compression ratio as a function of the acceptance angle of the transducer when using typical transducer parameters for a mid/high frequency linear transducer (e.g. 192 element transducer array with a 200 μm element pitch and center frequencies ranging from 4-8 MHz). The compression ratio as a function of acceptance angle is given for three different imaging frequencies. These plots demonstrate that raw channel data may be laterally Fourier compressed as compared with directly transferring raw channel data with compression ratios of greater than one, such as 2-3 (or higher). The amount of compression is driven by selected imaging optimization parameters. Where the ratio is close to or less than 1, then Fourier encoding is not as efficient as simply sending the raw channel data directly to the computer. For compression ratios larger than 1, the Fourier encoding with the beamformer effectively compresses the data and reduces the amount of data to be sent. For example, a transducer with a 30-degree acceptance angle that operates with a center frequency of 4 MHz is to be used. The compression ratio is close to 2:1, so beamformer Fourier compression in this situation would be optimal.

Where compression is used (e.g., Fourier encoded), the compressed channel data is transferred to the processor 62 and/or the memory 64. For example, the transfer is to a computer using a computer bus, such as a PCIExpress bus. The processor 62 of the computer uses software to inverse the Fourier transform to reconstruct the channel data to then perform delay-and-sum beamforming using software or applies temporal Fourier transformation for Fourier based beamformation using software. The compressed channel data may be used for any process by the processor 62.

The processor 62 is a control processor, filter, general processor, application specific integrated circuit, field programmable gate array, digital components, analog components, hardware circuit, combinations thereof and other now known or later developed devices for image processing to enhance an image. The processor 62 is configured, with computer code, firmware, and/or hardware, to generate ultrasound image information from the compressed and/or never compressed channel data.

In one embodiment, the processor 62 is part of a computer for implementing any ultrasound imaging using software. Beamformation, detection, scan conversion, mapping to display values, temporal filtering, spatial filtering, image enhancement, graphics generation, combinations thereof, and/or other ultrasound imaging process are performed by the processor 62. In alternative embodiments, separate components (e.g., beamformer, detector, filter, and/or scan converter) are provided and operate with or as part of the processor 62 for ultrasound imaging. The generated image information is ultrasound information representing the patient at any stage of processing (e.g., beamformed, detected, scan converted, and/or mapped to display values).

For dual-mode operation, the processor 62 is configured to generate image information in one or more imaging modes from channel data and/or beamformed data. The processor 62 may control the receive beamformer 56 to select between bypass, delay-and-sum beamformation, and/or compression. Where the receive beamformer 56 operates for conventional receive beamformation, the processor 62 receives the beamformed data and generates the image information. Where the processor 62 instead receives channel data without compression (e.g., beamformer 56 is bypassed), the processor 62 performs the beamforming from the channel data to generate the imaging information.

Where the receive beamformer 56 compresses the channel data, the processor 62 uses the compressed information to generate the imaging information. For example, electrical signals for one imaging mode are compressed by the beamformer. The processor 62 uses those compressed signals to generate imaging information.

In one embodiment, the compressed channel data is used for delay-and-sum beamformation. The compressed channel data is decompressed to reconstruct the channel data. An inverse Fourier transform is applied to the compressed electrical signals to reconstruct in a lossy or lossless manner the electrical signals from the elements. Using a set of reconstructed electrical signals from the different elements 70 over time, the processor 62 then applies a delay profile and an apodization profile to the reconstructed channel data and sums the results. Phasing or absolute delay may be used to implement the delay profile. Once beamformed, the processor 62 image processes the beamformed data, such as detecting, scan converting, and/or display mapping.

In another embodiment, the compressed channel data is used for other types of beamformation or image formation. Rather than use delay-and-sum beamformation, the echo return from different locations is derived using another process, such as a process in the domain of the basis function used to compress. For example, another Fourier transform is applied as a function of time or depth to the compressed channel data. Since the Fourier-based compression is lateral, the axial transform applied by the processor 62 results in a two-dimensional transformation. The two-dimensional transformed channel data in the frequency domain is used for beam or image formation, such as disclosed in U.S. Pat. No. 6,685,641.

FIG. 4 shows one representation of beamformation in the frequency domain. The compressed or Fourier encoded channel data is further Fourier transformed in time. The processor 62 multiplies the channel data in the frequency domain with a focusing function and then interpolates in the frequency domain from the results of the multiplication. Any of various interpolations may be used, such as a Stolt interpolation. The encoded data maps directly into the k-space of the beamformed image using conventional Stolt interpolation mappings. Where the encoding uses a complex apodization, the Stolt interpolation mapping is given by:

$$f'_x = f_x$$

$$f'_z = \frac{f}{c}\left(1 + \sqrt{1 - \lambda^2 f_x^2}\right).$$

Where the encoding uses a linear delay profile, a modified Stolt interpolation is used, as represented by:

$$f'_x = \frac{f \tan \theta_s}{c}$$

$$f'_z = \frac{f}{c}\left(1 + \sqrt{1 - \tan^2 \theta_s}\right).$$

After the interpolation, the processor 62 generates the imaging information by applying an inverse Fourier transformation. An inverse two-dimensional transformation is applied, resulting in beamformed values for each of different locations in the patient.

Other Fourier beamforming may be used. Since the data is in the frequency domain, any other k-space image formation or filtering may be applied. For example, magnetic resonance or computed tomography image formation or image filtering techniques using k-space data may be applied by the processor 62.

The processor 62 uses the imaging information to generate one or more ultrasound images. For example, B-mode images are generated. M-mode, color or flow mode, Doppler or spectral mode, or other modes of imaging may be used. In one embodiment using dual-modes of imaging, imaging from the different modes are combined into one image, such as an overlay of color flow on B-mode. The imaging information used for one mode is derived from beamformer-compressed channel data, and the imaging information used for another mode is derived from beamformed data or channel data received without compression by the processor 62. Both or all modes of imaging may be derived from beamformer-compressed channel data in other embodiments.

The display 60 is a monitor, LCD, LED, plasma, projector, printer, or other now known or later developed display device. The processor 62 generates display signals for the display 60. The display signals, such as RGB values, are output by the processor 62 to the display 60 or to a display buffer. The display 60 is configured to display an image representing the scanned region of the patient, such as a B-mode image. The image represents the scan region. The image is generated from at least some data that was at one point compressed by a delay-and-sum beamformer.

The memory 64 is a computer readable storage medium having stored therein data representing instructions executable by the programmed processor for ultrasound imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The memory 64 alternatively or additionally stores channel data, compressed channel data, reconstructed channel data, or other ultrasound data from any stage of processing. For example, the memory 64 receives the beamformer-compressed channel data from the receive beamformer over a bus and stores the data for access by the processor 62.

Figure 5:
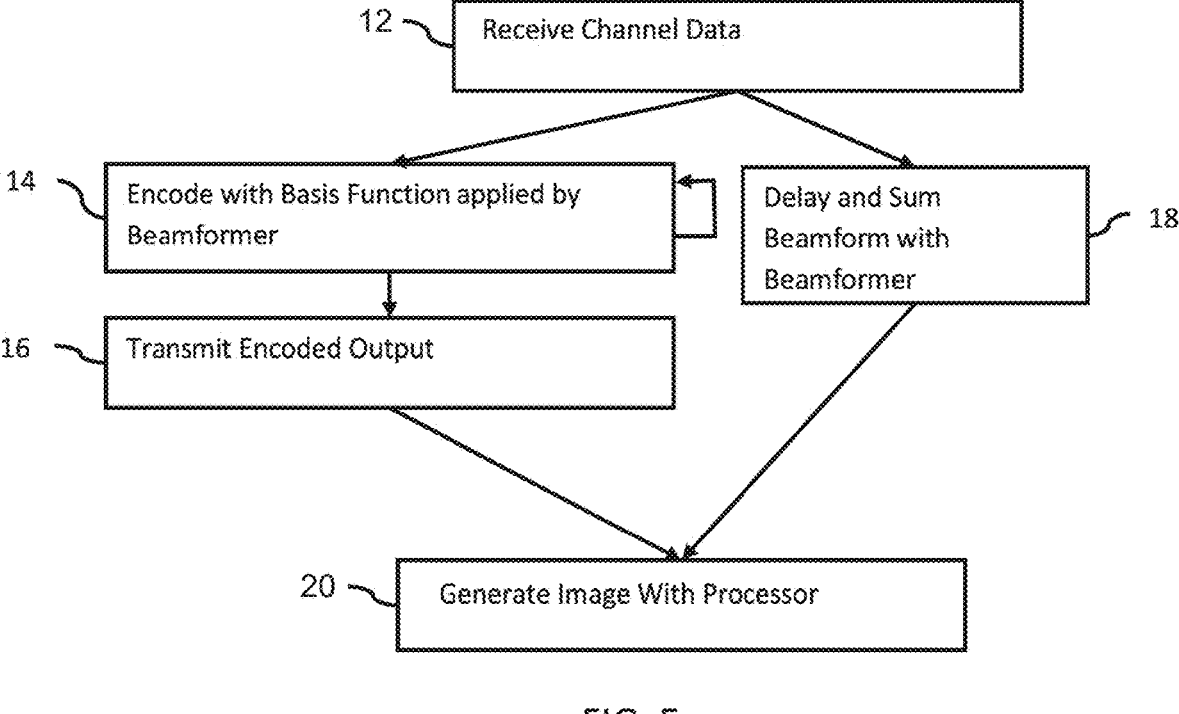
FIG. 5 is a flow chart diagram of one embodiment of a method for ultrasound beamformer-based channel data compression.

FIG. 5 shows one embodiment of a method for ultrasound beamformer-based channel data compression. Rather than using dedicated compression hardware for each receive channel, a receive beamformer may be used to laterally compress. The embodiment of FIG. 5 is directed to compressing channel data with a beamformer for subsequent beamformation after transfer of the compressed channel data and alternatively performing beamformation on channel data that is not compressed. In other embodiments, dual-mode operation is not provided, so just compression with subsequent image formation is performed.

Additional, different, or fewer acts may be provided. For example, act 18 is not provided. As another example, act 20 is not provided. Acts for other imaging operations, such as detection, filtering, scan conversion, and display mapping, may be performed.

The acts are performed in the order shown or a different order. For example, act 18 is interleaved with acts 14 and 16. Act 18 may be performed before, after, or in parallel (simultaneously) with acts 14 and/or 16.

In act 12, a beamformer receives channel data from elements of a transducer array. An ultrasound system acquires ultrasound data from a scan of tissue, blood, or other part of a patient. The ultrasound data represents the patient. A medical diagnostic ultrasound system applies electrical signals to a transducer, which then converts the electrical energy to acoustic energy for scanning a region of the patient. Waveforms at ultrasound frequencies are transmitted. Echoes are received and converted into electrical signals by elements of the transducer. Any type of scan, scan format, or imaging mode may be used. For example, harmonic imaging is used with or without added contrast agents. As another example, B-mode, color flow mode, spectral Doppler mode, M-mode, Elastography or other imaging mode is used.

Each element or group of elements outputs signals in a respective channel. Any number of channels is provided, such as 32, 64, 128, 256, or other number. The elements of the receive aperture each output to a separate or independent channel.

The channel signals may be amplified, such as with depth gain compensation. The channel signals may be converted from analog signals to digital samples. An analog-to-digital converter of each channel samples the element signals, creating channel data. The signals or samples may be filtered and/or buffered. Additional, different, or fewer processes may be applied, such as no conversion to digital for an analog beamformer.

In act 14, the receive beamformer encodes the channel data. Using the delay and apodization functions of each channel of a delay-and-sum beamformer, the channel data is encoded laterally across the array. Each channel contributes a sample to the encoding. The sample of each channel is delayed (e.g., delayed or phased) relative to other samples and apodized (e.g., changed in amplitude) relative to other samples for that time. Rather than or in addition to delay and apodization due to geometry of the element and location of interest in the patient for that time, the apodizations and delays applied to the samples of the different channels are based on a basis function for compression. The apodized and delayed samples from each channel are summed, providing for the lateral or across channel encoding.

Any appropriate basis function set may be used for encoding. For example, a wavelet or Fourier basis set is used. The basis functions provide for lossless or lossy recovery of the channel data. Delay-and-sum beamformation performed conventionally is not reversible. The channel data cannot be recovered. By encoding with basis functions, the channel data may be recovered or substantially recovered from the summed output of the beamformer. Substantially accounts for lossy compression, where 80% or more of the channel data may be recovered. The amount of compression loss is dependent on the number of basis functions used to encode the data. In the example of Fourier compression, the loss manifests itself in the form of poorer lateral image resolution. By applying an inverse transform or other basis function related inverse process, the channel data may be reconstructed, if desired.

In one embodiment, the beamformer implements a Fourier transform by encoding. The receive beamformer transforms samples from the lateral sampling domain of the channels into frequency data in the spatial frequency domain. For example, the encoding uses an apodization profile being unity and a linear delay profile. As another example, the encoding uses a geometry-based delay profile being zero and a complex apodization profile. The apodization and/or delay profiles and subsequent summation provide the encoding in the frequency domain.

The encoding act 12 may be repeated. The encoding is lateral across the array or channels for a given time. Echoes are received by each element over time. The encoding is performed for different times, encoding additional channel data as the channel data is received. The result is a set of laterally transformed data output over time by the receive beamformer.

In act 16, the encoded channel data is transmitted. The beamformer outputs the compressed data to a buffer, memory, interface, or communications path. The output is provided to a bus, cable, or other transmission line to a computer, processor, or memory. Any transmission format or packaging may be used, such as transmitting on a PCIExpress bus.

As the receive beamformer laterally encodes, the resulting data is transmitted. The transmission occurs upon each repetition over time. Alternatively, output data from one or more times is buffered and packetized with output data from a different time.

For software-based image processing, the computer receives transmission of the encoded channel data. The computer then performs any image processing. In one embodiment, the computer applies an inverse transform, such as an inverse Fourier transform, to recover the channel data. Software-based beamforming is performed by the processor using the recovered channel data. In another embodiment, the processor of the computer performs Fourier beamforming. Instead of recovering the channel data, a further Fourier transform is applied as a function of time. Multiplication with a focusing function and interpolation in frequency space are performed. The computer performs a two-dimensional, spatial inverse Fourier transform to determine the intensity or echo return for each of different locations in the patient distributed in one, two, or three dimensions. In other embodiments, different processes are applied by the computer to the compressed channel data.

The processor inverse transforms the frequency or other encoded data into object or real space. The processor generates an ultrasound image from an output of the inverse transformation. Any image processing may be used, such as beamformation, detection, estimation, filtering, scan conversion, and/or display mapping. The channel data or beamformed data is used to create an ultrasound image representing the scanned patient.

Any of the software processes applied by the processor may be easily changed without requiring a hardware change. The use of a beamformer for compression allows for use of a common component in ultrasound to compress data for transfer into or access by the computer and corresponding software-based image processing.

In act 18, the beamformer is provided for a dual-mode of operation. For some channel data, such as for some imaging modes, parameter settings, and/or imaging conditions, the beamformer applies delay-and-sum beamformation in object or real space. Instead of compressing, conventional beamformation is applied. The resulting beamformed data is transmitted to the computer or other image processor for generating an image. Alternatively, the beamformer is not used and the channel data is transmitted to the computer. The computer applies the beamformation using a software-based approach and a general processor.

Where dual-mode operation is provided, the compression by the beamformer and the beamforming or bypass of the beamformer by the channel data are interleaved. Channel data responsive to some transmissions is compressed, and channel data responsive to other transmissions is not compressed. The compression or no compression for an imaging session are interleaved by line, groups of line, or scan of a field of view basis.

In act 20, an image is generated. The processor or ultrasound system generates the image from the ultrasound data. The inverse transformed data and/or channel data not subjected to compression are used to generate an image on a display.

The generated image is a B-mode, color flow mode, M-mode, pulsed wave Doppler, contrast agent, harmonic, other ultrasound image, or combination thereof. The image represents the patient at a given time or over time. The image may represent one or more sample locations within the patient, such as a planar or volume region.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for ultrasound beamformer-based channel data compression, the method comprising:

receiving channel data from elements of a transducer array;

encoding the channel data laterally across the array with a delay and sum beamformer with a set of basis functions, wherein the encoding laterally across the array compresses data from multiple channels by delay and apodization profiles of the delay and sum beamformer, the delay and apodization profiles set to implement the basis functions, the basis functions implementing the encoding, an output of the encoding being a compression of the channel data from the multiple channels, the basis functions substantially enabling recovery of the channel data from each of the multiple channels from the output of the encoding, the channel data for the multiple channels being from the different elements and being used after application of the basis functions to encode the output;

repeating the encoding for additional channel data; and transmitting the output of the encoding.

2. The method of claim 1 wherein encoding the channel data laterally comprises encoding across channels such that each channel contributes data in the encoding.

3. The method of claim 1 wherein encoding with the delay and sum beamformer comprises encoding with an apodization profile being unity and a linear delay profile.

4. The method of claim 1 wherein encoding with the delay and sum beamformer comprises encoding with a geometry-based delay profile being zero and a complex apodization profile, the complex apodization profile implemented with phase shift.

5. The method of claim 1 wherein encoding with the basis functions comprises encoding with a Fourier transform implemented by the delay and sum beamformer.

6. The method of claim 1 wherein encoding with the basis functions comprises encoding for lossless or lossy recovery of the channel data.

7. The method of claim 1 wherein transmitting comprises transmitting to a software-based image processing, the software-based image processing including beamforming.

8. The method of claim 7 wherein the beamforming comprises Fourier beamforming, the Fourier beamforming comprising transforming the output as a function of time, interpolating, and inverse two-dimensional spatial Fourier transforming.

9. The method of claim 1 further comprising:

using the delay and sum beamformer to beamform other channel data, the use of the delay and sum beamformer to beamform interleaved with encoding with the delay and sum beamformer.

10. A method for ultrasound beamformer-based channel data compression, the method comprising:

sampling a plurality of channels of element signals;

transforming, by a receive beamformer, samples from a sampling domain into spatial frequency data in a frequency domain, the receive beamformer being a delay and sum beamformer, the transforming encoding the samples into a compression using delay and sum profiles of the receive delay and sum beamformer, the delay and sum profiles being used without reference to focal location and array geometry, which encoding is provided by the delay and sum profiles implementing basis functions, the basis functions implementing the encoding, which encoding is provided without referring to the focal location and without referring to the array geometry;

inverse transforming the frequency data; and generating, by a processor, an ultrasound image from an output of the inverse transforming.

11. The method of claim 10 wherein transforming comprises encoding the samples laterally across the array with the receive beamformer with a set of basis functions, the delay and sum profiles set to implement the basis functions, the basis functions substantially enabling recovery of the samples from an output of the encoding, the encoding being laterally across an array using the samples from the channels after application of the basis functions to encode the output.

12. The method of claim 10 wherein transforming comprises transforming across the channels such that each channel contributes data in the encoding.

13. The method of claim 10 wherein transforming comprises encoding with an apodization profile of the delay and sum profiles being unity and a delay profile of the delay and sum profiles being a linear delay profile.

14. The method of claim 10 wherein transforming comprises encoding with a geometry-based delay profile of the delay and sum profiles being zero and an apodization profile of the delay and sum profiles being a complex apodization profile, the complex apodization profile implemented with phase shift.

15. The method of claim 10 wherein transforming comprises encoding with a Fourier transform implemented by the receive beamformer.

16. The method of claim 10 wherein transforming comprises encoding for lossless or lossy recovery of the samples.

17. The method of claim 10 further comprising transmitting the frequency data to a software-based image processing, the software-based image processing including beamforming performing the inverse transforming.

18. The method of claim 17 wherein the beamforming comprises Fourier beamforming, the Fourier beamforming comprising transforming the frequency data as a function of time, interpolating, and inverse two-dimensional spatial Fourier transforming.

19. The method of claim 10 further comprising:

using the receive beamformer to beamform other samples with the delay and sum profiles, the use of the receive beamformer to beamform interleaved with transforming with the receive beamformer.

* * * * *